United States Patent
Meskens

(10) Patent No.: US 10,357,659 B2
(45) Date of Patent: Jul. 23, 2019

(54) IMPLANT CHARGING PROTECTION

(71) Applicant: Cochlear Limited, Macquarie University, NSW (AU)

(72) Inventor: Werner Meskens, Mechelen (BE)

(73) Assignee: COCHLEAR LIMITED, Macquarie University (AU)

( * ) Notice: Subject to any disclaimer, the term of this patent is extended or adjusted under 35 U.S.C. 154(b) by 76 days.

(21) Appl. No.: 15/598,545

(22) Filed: May 18, 2017

(65) Prior Publication Data

US 2018/0333584 A1    Nov. 22, 2018

(51) Int. Cl.
| | |
|---|---|
| A61N 1/00 | (2006.01) |
| A61N 1/378 | (2006.01) |
| H02J 50/12 | (2016.01) |
| A61N 1/36 | (2006.01) |

(52) U.S. Cl.
CPC ............ A61N 1/3787 (2013.01); H02J 50/12 (2016.02); *A61N 1/36036* (2017.08)

(58) Field of Classification Search
CPC .......................... A61N 1/3787; A61N 1/36032
See application file for complete search history.

(56) References Cited

U.S. PATENT DOCUMENTS

| | | | |
|---|---|---|---|
| 5,279,292 A | 1/1994 | Baumann et al. | |
| 2012/0053657 A1* | 3/2012 | Parker .................. | A61N 1/3787 607/61 |
| 2013/0165993 A1 | 6/2013 | Aghassian et al. | |
| 2014/0025140 A1* | 1/2014 | Lui ...................... | A61N 1/3787 607/61 |

FOREIGN PATENT DOCUMENTS

| | | |
|---|---|---|
| KR | 1020050039445 A | 4/2005 |
| WO | 2004002572 A1 | 1/2004 |

OTHER PUBLICATIONS

"ICNIRP Guidelines for Limiting Exposure to Time-Varying Electric and Magnetic Fields (1 Hz-100 kHz)", International Commission on Non-Ionizing Radiation Protection, Published in: Helath Physics 99 (6):818-836; 2010, Dec. 2010, vol. 99, No. 6, 20 pages.
International Search Report and Written Opinion in corresponding International Application No. PCT/IB2018/053257, dated Oct. 23, 2018.

* cited by examiner

*Primary Examiner* — George Manuel
(74) *Attorney, Agent, or Firm* — Edell, Shapiro & Finnan, LLC

(57) ABSTRACT

An external charger includes at least one coil antenna, comprised of one or more loops of wire, and a coil excitation system connected to the at least one coil antenna. The coil excitation system is configured to drive the one or more loops or wire with alternating current to generate a magnetic field that is configured to induce current in at least one implantable coil of an implantable medical device. The external charger also includes an electrical non-conductive safeguard enclosure disposed around the one or more loops of wire. The coil safeguard enclosure is configured to prevent the implantable medical device from being positioned within a predetermined vicinity of the one or more loops of wire.

38 Claims, 13 Drawing Sheets

Hx FIELD COMPONENT IN FUNCTION OF x AND z
Hx FIELD - LOOP RADIUS 160mm

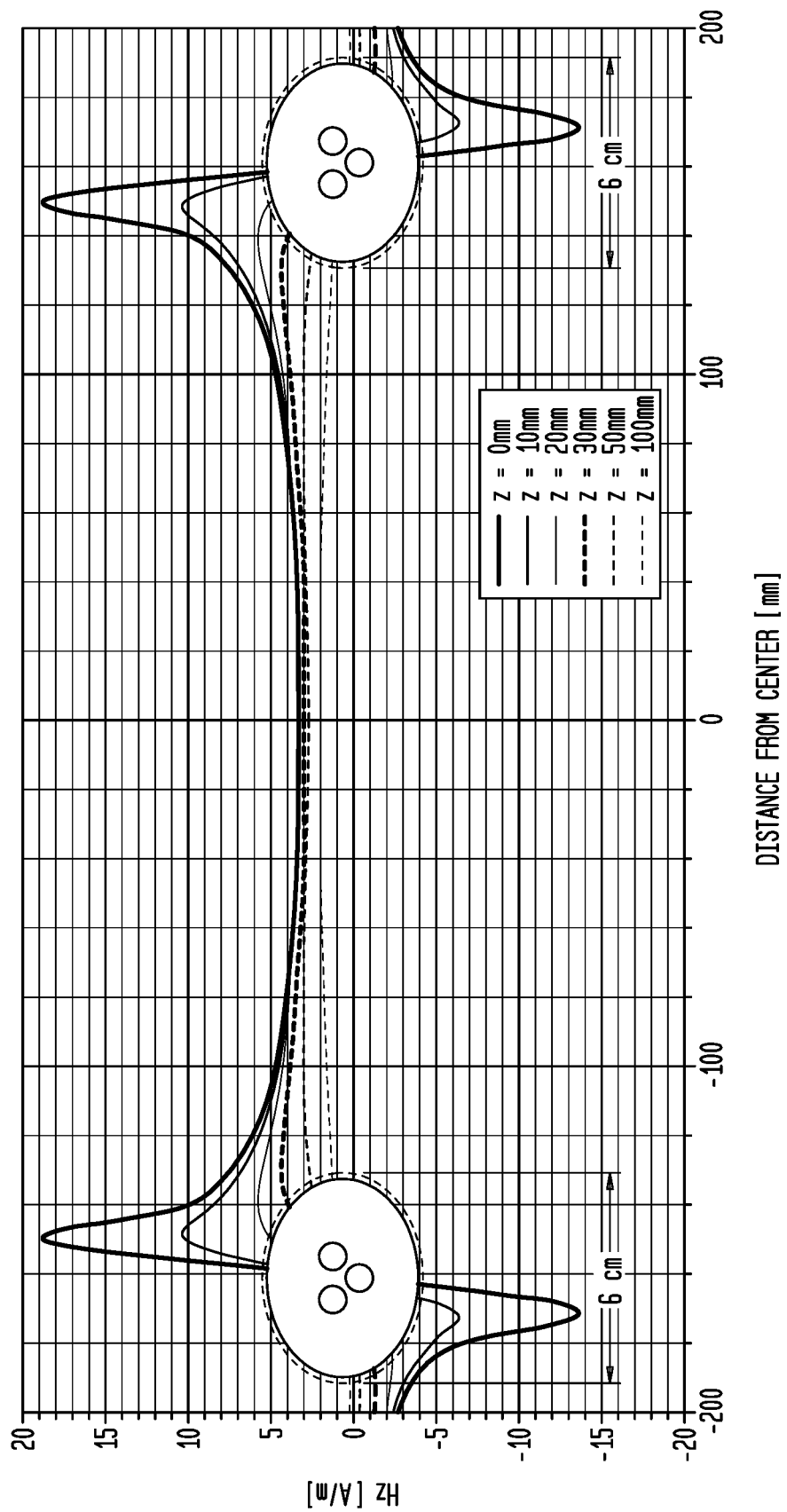

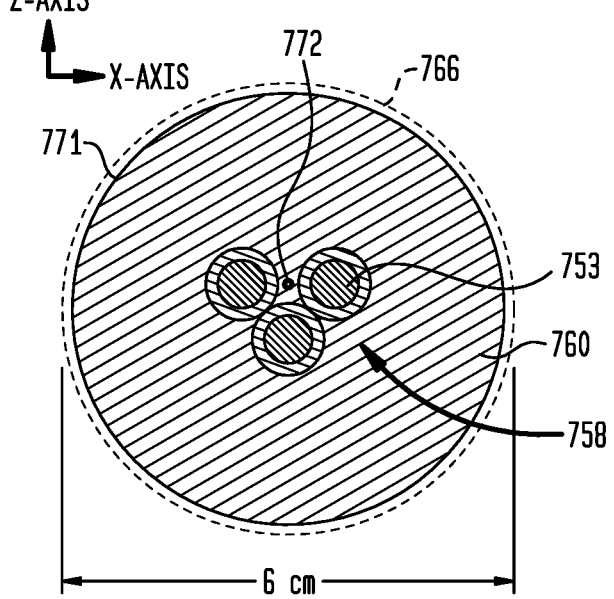
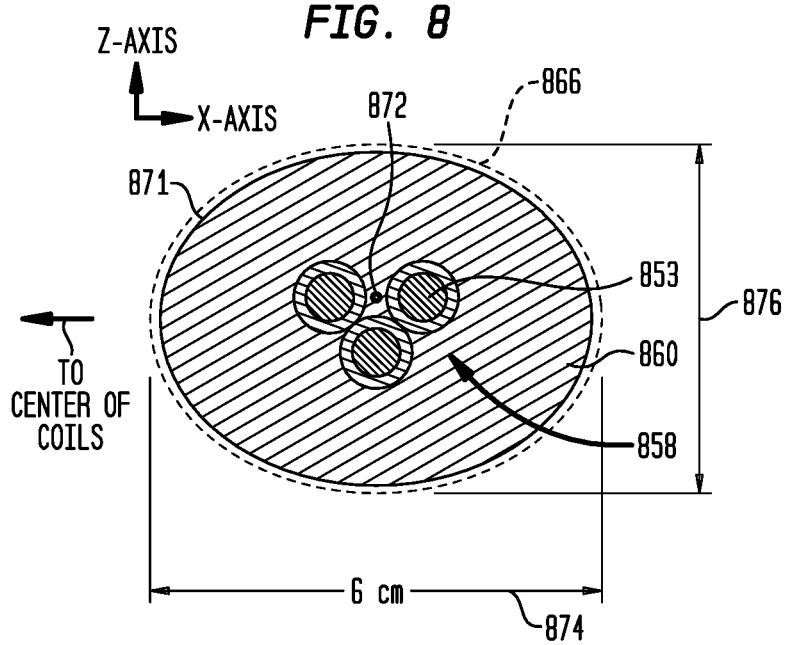

IMPLANT CHARGING PROTECTION

BACKGROUND

Field of the Invention

The present invention relates generally to a charging of implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or are employed to investigate, replace or modify the anatomy or a physiological process. Many of these functional components utilize power and/or data received from external components that are part of, or operate in conjunction with, the implantable medical device.

SUMMARY

In one aspect an external charger for an implantable medical device is provided. The external charger comprises: at least one coil antenna comprising one or more loops of wire; a coil excitation system connected to the at least one coil antenna, wherein the coil excitation system is configured to drive the one or more loops or wire with alternating current to generate a magnetic field that is configured to induce current in at least one implantable coil of the implantable medical device; and an electrical non-conductive safeguard enclosure disposed around the one or more loops of wire to prevent the implantable medical device from being positioned within a predetermined vicinity of the one or more loops of wire.

In another aspect an implantable hearing prosthesis pillow charger is provided. The pillow charger comprises: at least one coil antenna configured to emit one or more magnetic fields; and an electrical non-conductive safeguard enclosure disposed around the at least one coil antenna to shield the implantable hearing prosthesis from exposure to densities of the one or more magnetic fields that exceed a predetermined threshold.

In another aspect, an external charger for an implantable hearing prosthesis implanted in the head of a recipient is provided. The external charger comprises: at least one coil antenna comprising a wire bundle; a coil excitation system configured to drive the one or more loops or wire with alternating current and cause the at least one coil antenna to emit a magnetic field; and an electrical non-conductive safeguard enclosure arranged around the wire bundle to maintain a minimum separation distance between the head of the recipient and the wire bundle.

BRIEF DESCRIPTION OF THE DRAWINGS

Embodiments of the present invention are described herein in conjunction with the accompanying drawings, in which:

FIGS. 5A and 5B are graphs illustrating the strength of magnetic fields generated by a coil antenna, in accordance with embodiments presented herein;

FIG. 7 is a schematic cross-sectional diagram illustrating a cross-sectional shape for a coil safeguard enclosure embedding three loops of wire, in accordance with certain embodiments presented herein;

FIG. 8 is a schematic cross-sectional diagram illustrating another cross-sectional shape for a safeguard coil safeguard enclosure embedding three loops of wire, in accordance with certain embodiments presented herein;

DETAILED DESCRIPTION

Presented herein are external charging devices (external chargers) for an implantable medical device (implant). An external charger in accordance with embodiments presented herein include at least one coil antenna, comprised of one or more loops of wire, and a coil excitation system connected to the at least one coil antenna. The coil excitation system is configured to drive the one or more loops of wire with alternating current to generate a magnetic field that is configured to induce current in at least one implantable coil of an implantable medical device. The external charger also includes an electrical non-conductive safeguard enclosure disposed around the one or more loops of electrical conductive wire. The safeguard enclosure is a layer or volume that is configured to prevent the implantable medical device from being positioned within a predetermined vicinity of the one or more loops of wire.

External chargers in accordance with embodiments presented herein may be used with a number of different types of implantable medical devices (implants). However, merely for ease of illustration, the techniques presented herein are primarily described with reference to charging one type of implantable medical device, namely a cochlear implant. It is to be appreciated that the external chargers presented herein may be used with any other partially or fully implantable medical device now known or later developed, including other auditory prostheses, such as auditory brainstem stimulators, electro-acoustic hearing prostheses, bimodal hearing prostheses, etc., and/or other types of medical devices, such as pain relief implants, pacemakers, etc.

Figure 1:
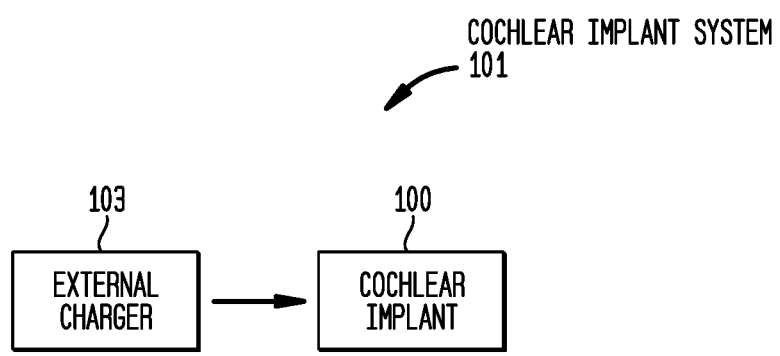
FIG. 1 is a block diagram illustrating a cochlear implant system, in accordance with embodiments presented herein.

FIG. 1 is a block diagram of an exemplary system 101 that includes a cochlear implant 100 and an external charging device 103, in accordance with embodiments presented. The external charging device 103 is sometimes referred to herein as an external charger. The external charger 103 may have a number of different forms, such as a pillow charger, charging mat, neck pillow, etc.

As described below, the cochlear implant 100 comprises a rechargeable battery (not shown in FIG. 1) that is configured to be recharged using power signals received from the external charger 103 via an inductive radio frequency (RF) link. Also as described below, the external charger 103 is a device that includes one or more coil antennas that emits a magnetic field. Each of the coil antennas are formed by a plurality of "wire loops" or "windings" of electrical conductors that, in the embodiments presented herein, are enclosed in an electrical non-conductive safeguard enclosure, sometimes referred to herein as a "coil safeguard enclosure." As described further below, the coil safeguard enclosure is configured to prevent the cochlear implant 100 from being positioned within a predetermined vicinity of the one or more loops of wire within the coil antenna.

Figure 2A:
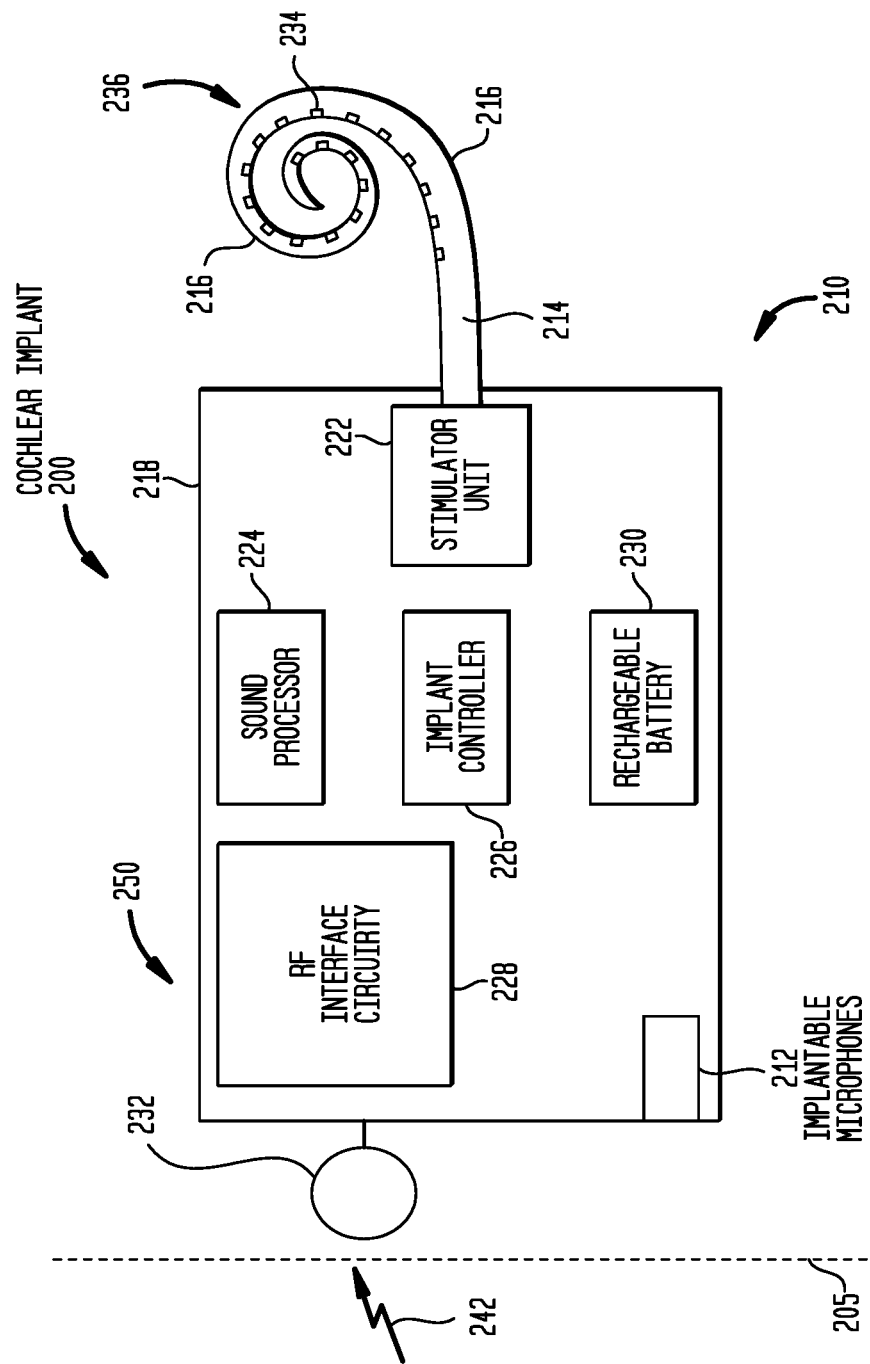
FIG. 2A is block diagram of a cochlear implant, in accordance with embodiments presented herein.
Figure 2B:
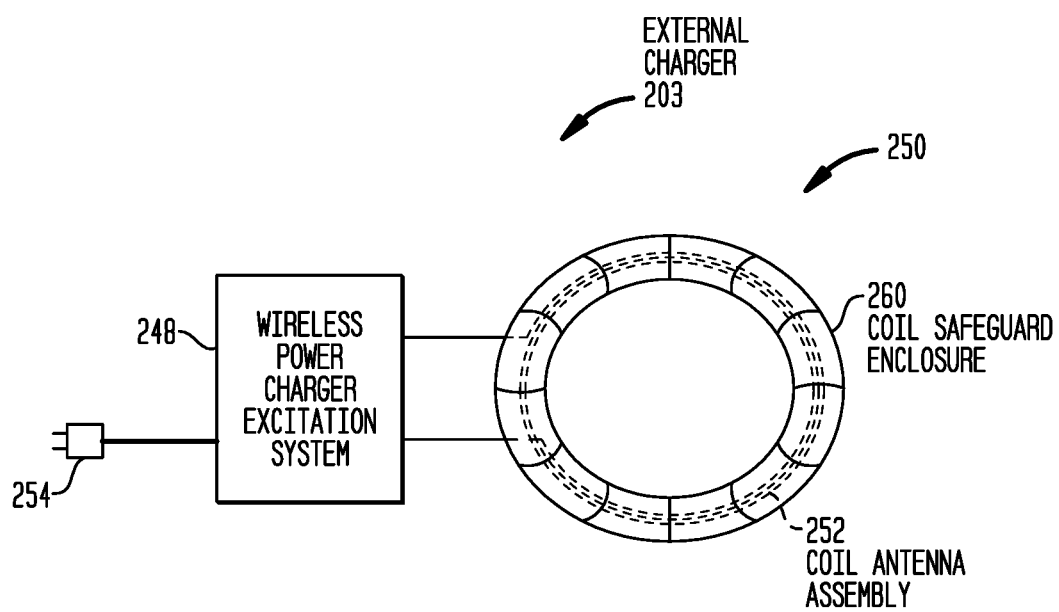
FIG. 2B is a block diagram of an external charger, in accordance with embodiments presented herein.

It is to be appreciated that the cochlear implant 100 of FIG. 1, as well as the external charger 103 of FIG. 1, may each have a number of different arrangements. FIG. 2A is a block diagram illustrating one example arrangement for the cochlear implant 100, referred to as cochlear implant 200. FIG. 2B is a block diagram illustrating one example arrangement for external charger 103, referred to as external charger 203, in accordance with embodiments presented herein.

Referring first to FIG. 2A, the cochlear implant 200 is a totally implantable cochlear implant where all components of the cochlear implant are configured to be implanted under the skin/tissue 205 of a recipient. Because all components are implantable, cochlear implant 200 operates, for at least a finite period of time, without the presence of an external device (e.g., without external charger 203).

Cochlear implant 200 includes an implant body (main module) 210, a lead region 214, and an elongate intra-cochlear stimulating assembly 216. The implant body 210 generally comprises a hermetically-sealed housing 218 in which a stimulator unit (stimulation electronics) 222, a sound processor 224, an implant controller 226 (i.e., battery and power management component or battery processor), RF interface circuitry 228, and a rechargeable battery 230 are disposed. It is to be appreciated that cochlear implant 200 may include one or more other components that, for ease of illustration, have been omitted from FIG. 2A.

The implant body 210 also includes one or more implantable microphones 212 and an internal/implantable coil 232 that are each typically located external to the housing 218. The implantable coil 232 is connected to elements within the housing 218 via hermetic feedthroughs (not shown in FIG. 2). Implantable coil 232 is typically a wire antenna coil comprised of multiple turns of electrically insulated single-strand or multi-strand platinum or gold wire. The electrical insulation of implantable coil 232 is provided by a flexible molding (e.g., silicone molding), which is not shown in FIG. 2A. Generally, a magnet is fixed relative to the implantable coil 232 for magnetic coupling with a magnet in an external device.

Elongate stimulating assembly 216 is configured to be at least partially implanted in the recipient's cochlea (not shown) and includes a plurality of longitudinally spaced intra-cochlear electrical stimulating contacts (electrodes) 234 that collectively form a contact array 236 for delivery of electrical stimulation (current) to the recipient's cochlea. Stimulating assembly 216 extends through an opening in the cochlea (e.g., cochleostomy, the round window, etc.) and has a proximal end connected to the stimulator unit 222 via the lead region 214 and a hermetic feedthrough (not shown in FIG. 2). Lead region 214 includes one or more conductors (wires) that electrically couple the electrodes 234 to the stimulator unit 222. In this way, cochlear implant 200 electrically stimulates the recipient's auditory nerve cells, bypassing absent or defective hair cells that normally transduce acoustic vibrations into neural activity, in a manner that causes the recipient to perceive one or more components of the received sound signals.

The one or more implantable microphones 212 are configured to detect/receive input sound signals that are provided to the sound processor 224 by the RF interface circuitry 228. The sound processor 212 is configured to execute sound processing and coding to convert the received sound signals into output signals for use by the stimulator unit 222 in delivering electrical stimulation (current) to the recipient via electrodes 234.

The implantable coil 232 enables cochlear implant 200 to receive power/current signals from an external charger (e.g., external charger 203) via an RF link, sometimes referred to herein as an inductive power link, which is represented in FIG. 2A by arrow 242. The rechargeable battery 230 is configured to store the energy needed to power the other elements of the cochlear implant 200, as well as to provide the current needed to electrically stimulate the recipient's cochlea. The RF interface circuitry 228 is configured to operate under the control of the implant controller 226 and contains the necessary switches so as to charge the rechargeable battery 230 using the power received via inductive power link 242.

Referring next to FIG. 2B, the external charger 203 comprises a wireless power charger excitation system 248, sometimes referred to herein as a coil excitation system, and a coil antenna assembly 207 that includes one or more coil antennas 250 that emit a magnetic field. For ease of description, external chargers in accordance with embodiments presented herein are primarily described with reference to the use of a single coil antenna. However, it is to be appreciated that external chargers in accordance with embodiments presented herein may include a plurality of coil antennas.

In the embodiment of FIG. 2B, the coil antenna 250 is formed by a plurality of "loops" or "coils" 252 of wire, where the plurality of loops are sometimes collectively referred to as a "wire-loop bundle." The external charger 203 also comprises an electrical connection 254 to a power source. In one example, the electrical connection includes a galvanic isolation element or a transformer (not shown in FIG. 2B) to insulate the power source from the electronics of the external charger 203. The electrical connection 254 may also include a 12V DC adapter (not shown in FIG. 2B).

The coil excitation system 248 comprises one or more elements (e.g., a waveform generator, one or more amplifiers, tuning capacitors, etc.) that are used to drive the coil antenna 250 with an alternating current signal so that the coil antenna 250 will emit a corresponding magnetic field. That is, when driven by the coil excitation system 248, the wire coils 252 hold varying electrical currents that generate/emit magnetic fields that can be used to charge the cochlear implant 200. When the implantable coil 232 is placed in proximity to the coil antenna 250, the magnetic fields emitted by the coil antenna 250 pass through the implantable coil 232. As such, a current is induced in the implantable coil 232 that, in turn, can be used to charge the rechargeable battery 232. The amount of current induced in the implantable coil 232 is related to the total magnetic flux enclosed by the area of the implantable coil at a given time (i.e., the total magnetic flux linking a winding is proportional to the current through that winding). In certain embodiments, the coil excitation system 248 operates without feedback from the cochlear implant 200 (i.e., the magnetic field is generated without feedback from the cochlear implant).

Although the magnetic fields emitted by an external charger are needed to charge the cochlear implant, there is also a potential in conventional arrangements that these magnetic fields (H fields) could damage the cochlear implant. That is, the magnetic fields generated by an external charger are not always adapted to the position of the implant and the implant can be too close or too far away from the coil antenna(s). In addition, coil antenna(s) emit relatively high magnetic fields, especially in the close vicinity of the wire coils. These excessive fields in close vicinity to the wire coils have the potential to damage/destruct elements of an implant and/or to cause heat within the cochlear implant. For example, overvoltage and/or too high induced currents at an implantable coil may destruct elements of the RF interface circuitry (e.g., the implant rectifier circuit, the tranzorbs, the voltage clamps or even other passive components) in an implant. Too high RF voltages induced over an implantable coil may also have a negative effect on safety of the recipient. In many instances, there is no back link communication channel from the implant to the external charger that is able to request the external charger to increase or decrease its wire-loop current.

An external charger in accordance with embodiments presented herein, such as external charger 203, is configured with a safety mechanism to ensure that the charger does not damage an implant that is being charged thereby and does so without the need for a back link/channel from the implant to the external charger. More particularly, referring to the specific arrangement of FIG. 2B, an electrical non-conductive safeguard enclosure (coil safeguard enclosure) 260 is disposed around the wire coils 252. Since the wire coils 252 are located within the coil safeguard enclosure 260, the wire coils 252 are shown in FIG. 2B using dashed lines.

As described further below, the coil safeguard enclosure 260 is configured to prevent any element of the cochlear implant 200 from being positioned within a predetermined vicinity of the wire coils 252 (e.g., to maintain a minimum separation distance between the head of the recipient and a center of the wire coils 252 where the magnetic field (H) is too excessive). In one form, the coil safeguard enclosure 260 is configured to shield the cochlear implant 200 from exposure to densities of the one or more magnetic fields that exceed a predetermined threshold. Further details of the coil safeguard enclosures in accordance with embodiments presented herein are provided below with reference to FIGS. 3A-3C.

Figure 3A:
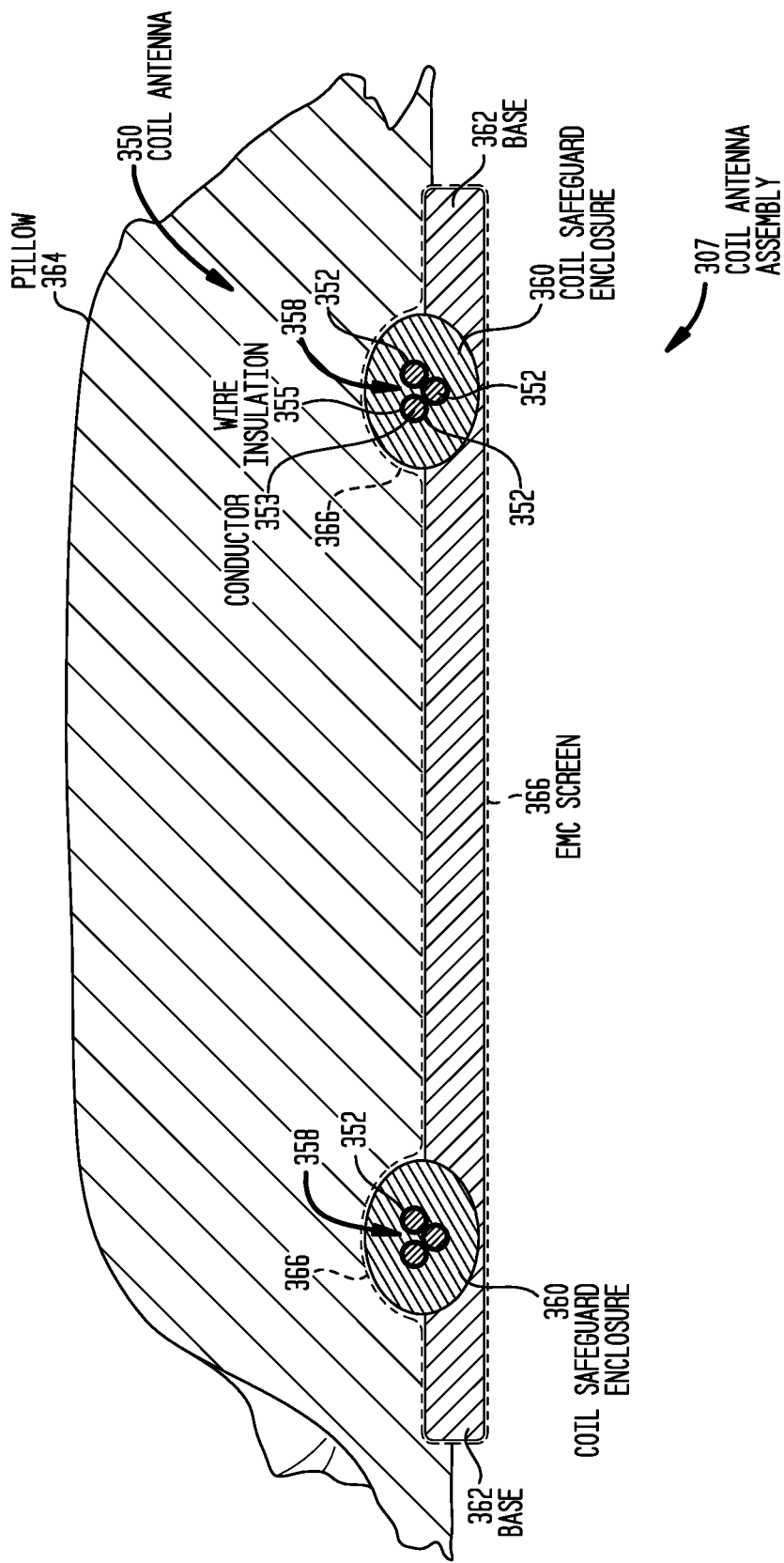
FIG. 3A is a cross-sectional layout diagram of the coil antenna assembly of an external charger, in accordance with certain embodiments presented herein.
Figure 3B:
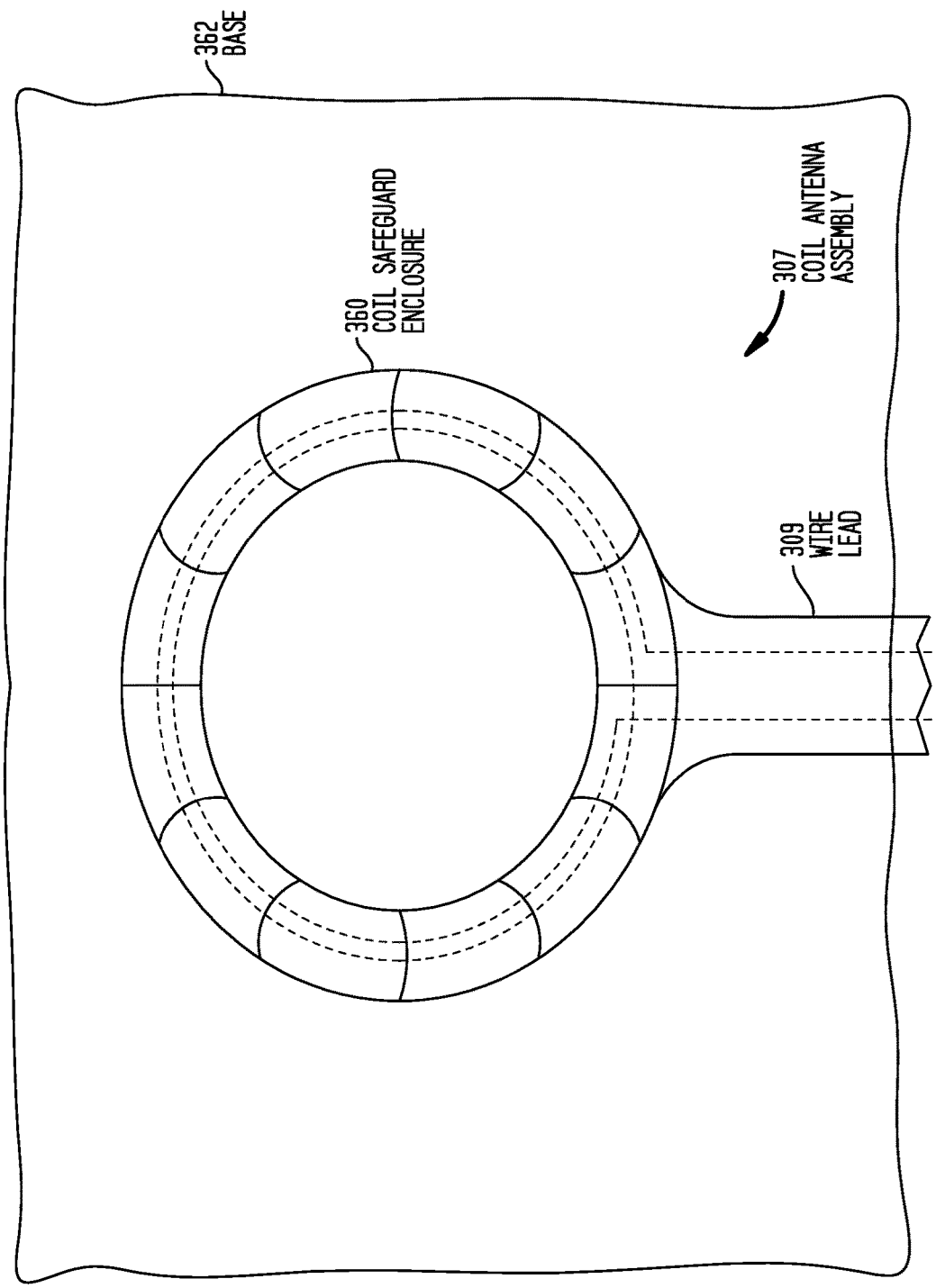
FIG. 3B is a top view of the coil antenna assembly of the external charger of FIG. 3A.
Figure 3C:
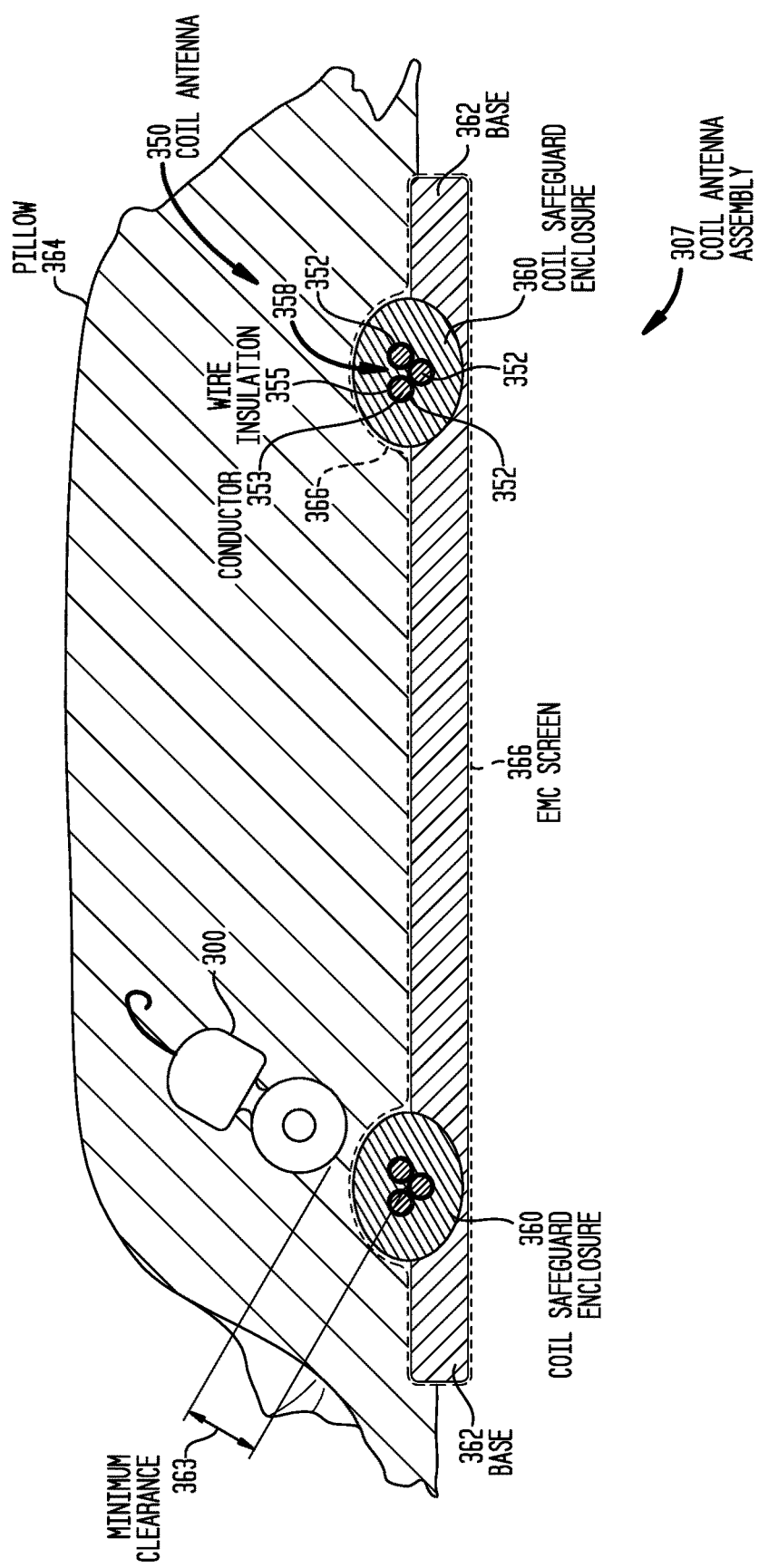
FIG. 3C is cross-sectional layout diagram of the coil antenna assembly of the external charger of FIG. 3A, which is shown with an implantable medical device.

More specifically, FIG. 3A is a cross-sectional layout diagram of one of the embodiments of a coil antenna assembly 307 of an external charger in the form of a pillow charger. FIG. 3B is a top view of the coil antenna assembly 307 of the external charger, while FIG. 3C is another cross-sectional layout drawing illustrating the coil antenna assembly 307 with an implantable medical device (implant 300). For ease of description, FIGS. 3A-3C will be described together. Although FIGS. 3A-3C illustrate a pillow charger, it is to be appreciated that external chargers in accordance with embodiments presented herein may be integrated in other structures, such as a chair (e.g., relax chair), a mattress, etc.

In the example embodiment of FIGS. 3A and 3B, the coil antenna assembly 307 is electrically similar to the coil assembly of the external charger 203 of FIG. 2B. The coil antenna assembly 307 is connected to a coil excitation system (not shown) via a wire lead 309. The coil excitation system is used to drive a coil antenna 350 with an alternating current signal so that the coil antenna 350 will emit a corresponding magnetic field. The coil antenna assembly 307 also comprises a base (e.g., mat) 362 that is formed from a relative soft material. In one embodiment, the base 362 is formed from a foam material.

Similar to the above arrangement, the coil antenna 350 is formed by a plurality of loops 352 of conductor/wire 353, where the plurality of coils are sometimes collectively referred as a wire-loop bundle 358. As shown, a thin layer of wire insulation 355 is disposed circumferentially around the outer surface of the wire 353. In addition, an electrical non-conductive safeguard enclosure 360 is disposed around the plurality of wire coils 352 (i.e., around the wire-loop bundle 358). In general, the coil safeguard enclosure 360 is a substantially thick (relative to the wire 353) protective layer or jacket around wire-loop bundle 358 that is configured to substantially reduce or eliminate the possibility that an implant (e.g., implant 300) could be placed in the close vicinity of the wires 353 in which the magnetic field 'H' is sufficiently high/excessive so as to potentially damage the implant. FIG. 3C illustrates that the coil safeguard enclosure 360 is configured to maintain a minimum clearance (distance) 363 between implant 300 and a median point 372 of the wire-loop bundle 353 in one or more directions/dimensions. As used herein, the median point 372 of the wire-loop bundle 353 refers to a median point of the collective wires 353 at a given tangential location (i.e., at a discrete point on the coil antenna 250), rather than the median of the coil antenna itself (i.e., the median point of the circle defined by the coils of wire).

In embodiments of FIGS. 3A-3C, the coil safeguard enclosure 360 is partially disposed in, and extends from, the base 362. Also as shown in FIGS. 3A and 3C, a pillow 364 may be located above the coil safeguard enclosure 360. As such, in the embodiments of FIGS. 3A-3C, the coil antenna 350 and the coil safeguard enclosure 360 are disposed between the base 362 and the pillow 364. For ease of illustration, the pillow 364 has been omitted from the top view of FIG. 3B.

The coil safeguard enclosure 360 is formed from at least one electrical non-conductive material that is operable/configured to maintain a minimum clearance or volume around the coils 352 of the wire 353 in one or more directions/dimensions so as to protect implant 300 from one or more of overvoltage or excessive induced current caused by components of the magnetic field in close proximity to the coils 352. In certain embodiments, the at least one electrical non-conductive material is a substantially rigid material that cannot be compressed in response to in-use external forces, such as when a recipient places his/her head on the pillow 364. In these embodiments in which the at least one electrical non-conductive material is rigid, the safeguard enclosure 360 may have one or more outer dimensions that correspond to the minimum clearance or volume around the coils 352 of the wire 353 that is needed to protect an implant from one or more of overvoltage or excessive induced current. In other embodiments, the at least one electrical non-conductive material is a partially compressible material having a minimum compressed outer dimension. In these embodiments, the minimum compressed outer dimension corresponds to the minimum clearance or volume around the coils 352 of the wire 353 that is needed to protect implant 300 from one or more of overvoltage or excessive induced current.

In certain embodiments, the coil safeguard enclosure 360 can be formed form a plurality of different materials with different properties. For example, the coil safeguard enclosure 360 could be formed by different layers of materials each having a different bulk modulus (i.e., with different grades of compressibility), where more compressible/softer material is used as the outer layer(s) and less compressible materials are used as the inner layer(s).

As shown in FIG. 3A, in certain embodiments an electromagnetic compatibility (EMC) screen 366 may be disposed so as to surround at least the coil safeguard enclosure 360. However, in the example of FIG. 3A, the EMC screen 360 is shown also surrounding the base 362. The optional EMC screen 366 is configured to block harmonics at certain frequencies (e.g., above 30 MHz) that could potentially interfere with other devices. The EMC screen 360 is a type of fine electrical conductive grid that enables the passage of the magnetic (H) field, but blocks radiated components above certain frequencies. In further embodiments, the coil safeguard enclosure 360 itself may include material with a higher permeability than air that is lossy for harmonics generated by the coil excitation system that drives the coil antenna 350. These embodiments may also improve the EMC of the external charger (i.e., block radiated components above certain frequencies).

As shown in FIG. 3A, in certain embodiments the external charger may comprise a layer 365 (sheet, washer, etc.) of magnetic material disposed between the coil antenna assembly 307 and a support structure (e.g., a mattress). The magnetic layer 365 has a permeability that is higher than air and is configured to guide the magnetic field lines away from the support structure (e.g., magnetic layer guides the magnetic field lines away from the mattress in case the mattress has electrical conductive parts and thus avoiding Eddy Current losses inside the conductive parts of the mattress). In certain embodiments, the coil antenna assembly 307 may further comprise pieces of magnetic material having a higher permeability than air which are disposed nearby, below or on top of the coil antenna to guide the magnetic field lines. These distributed pieces or slices of ferrite sheet make the H-field more uniform and would even decrease the maxima of H-field levels even more.

FIGS. 3A-3C illustrate embodiments in which the coil antenna assembly 307 is separate from the pillow 364 (e.g., just below the pillow partially inside a soft base/mat). It is to be appreciated that this embodiment is illustrative and that external chargers in accordance with certain embodiments presented herein may reside inside a pillow (e.g., a customized pillow).

Figure 4A:
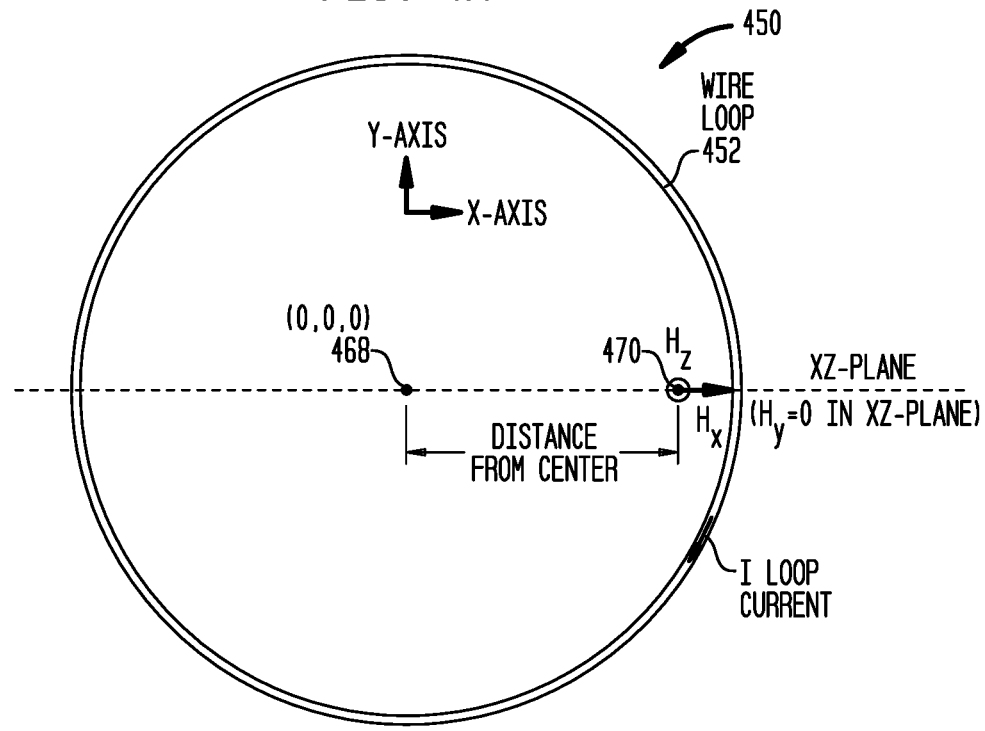
FIG. 4A is a top view of an example coil antenna, in accordance with certain embodiments presented herein.
Figure 4B:
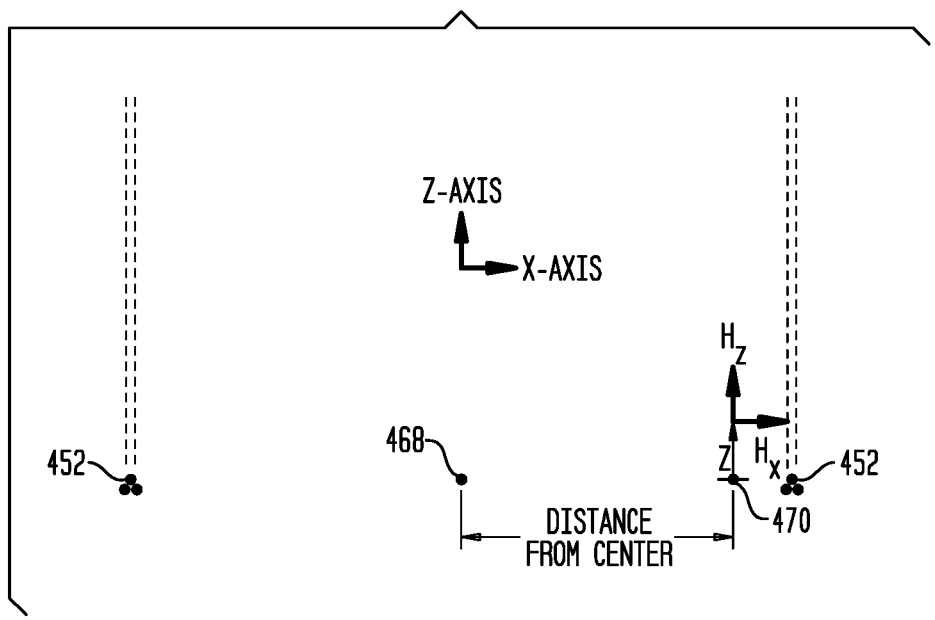
FIG. 4B is a schematic diagram illustrating a cross-sectional view of the coil antenna of FIG. 4A.

FIGS. 4A and 4B are schematic top and cross-sectional views, respectively, of an example coil antenna 450, in accordance with embodiments presented herein. For ease of illustration, FIGS. 4A and 4B are described with reference to a three-dimensional Cartesian coordinate system formed by three coordinate axis, referred to as the "X-axis," the "Y-axis," and the "Z-axis," which are shown in FIGS. 4A and 4B.

In the examples of FIGS. 4A and 4B, the coil antenna 450 comprises three (3) wire loops 452 that are each disposed in XY planes (planes formed by the X-axis and the Y-axis). As such, FIG. 4A illustrates a view of the coil antenna 450 in the XY plane, while FIG. 4B is a cross-sectional view of the coil antenna in the XZ plane. The coil antenna 450 (i.e., the wire loops 452) have a collective center location/point 468, which is located at Cartesian point (0,0,0) of the X, Y, and Z-axis.

FIGS. 4A and 4B also illustrate a point 470 that is positioned a distance from the center point 468 where magnetic fields (H-fields) are generated. FIGS. 4A and 4B schematically illustrate H-fields generated in the XZ-plane.

Figure 5A:
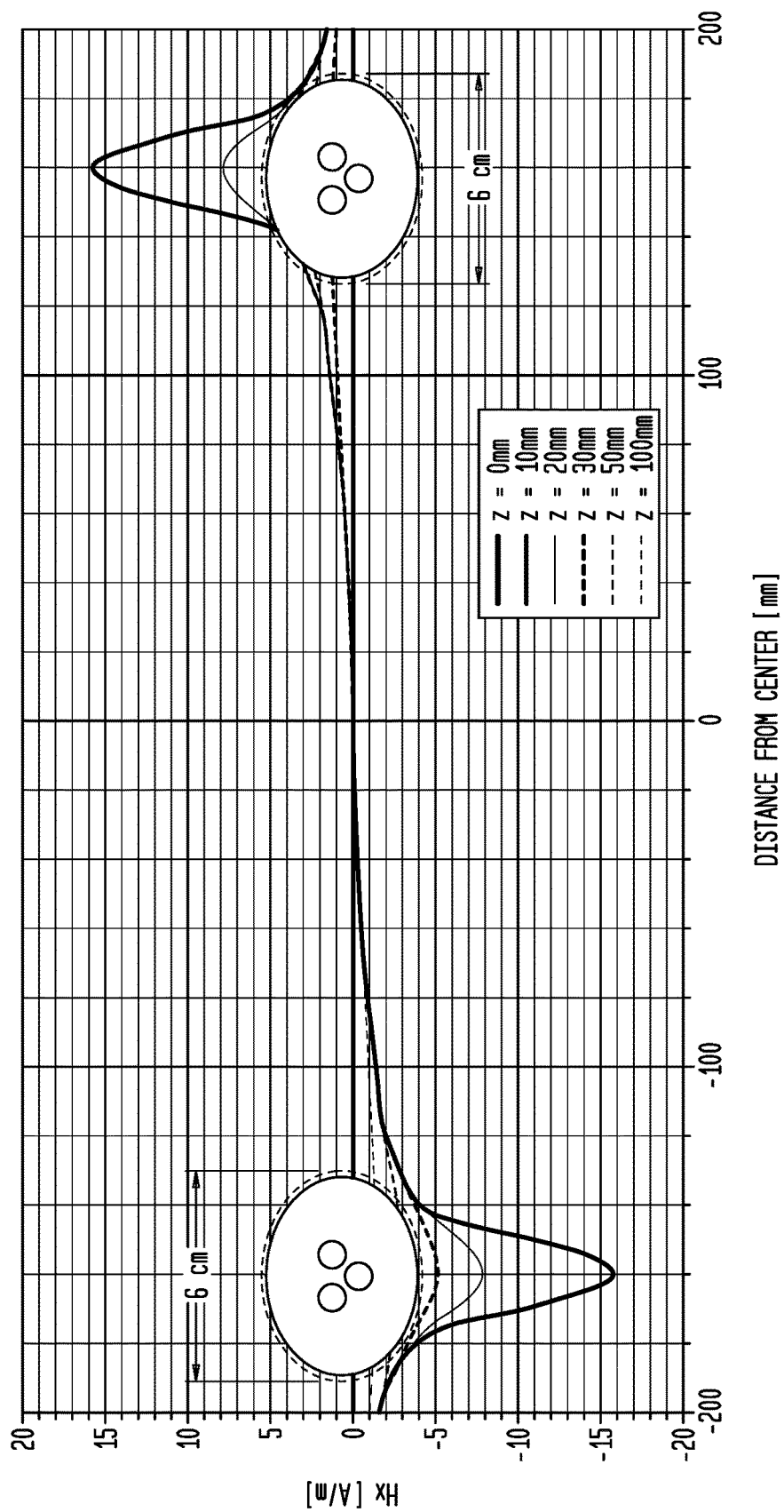

As noted above, a coil antenna, such as coil antenna 450, is driven with a current that causes the coil antenna to emit one or more magnetic fields (H-fields). FIGS. 5A and 5B are graphs illustrating the H-fields generated by the coil antenna 450 at different distances from the center point 468 (0,0,0). In particular, FIG. 5A illustrates the magnetic field strength projected on the X-axis in the XZ-plane, measured in amperes per meter (A/m), denoted as Hx. FIG. 5B illustrates the magnetic field strength projected on the Z-axis in the XZ-plane, again measured in A/m, denoted as Hz. The magnetic field component on the Y-axis ($H_y$) is zero in the XZ-plane.

Figure 6:
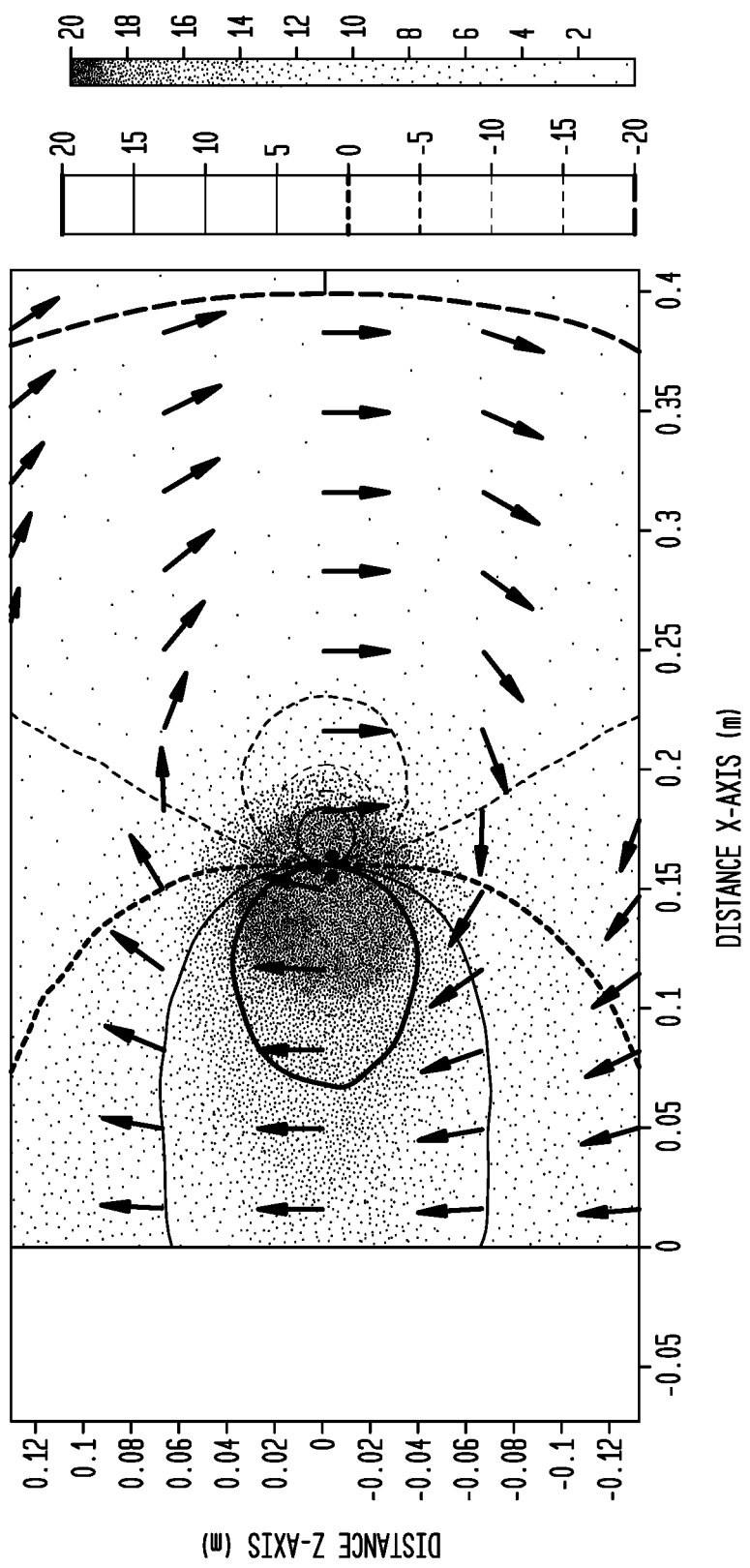
FIG. 6 is a schematic diagram illustrating field distributions for a normalized magnetic field of a coil antenna, in accordance with embodiments presented herein.

FIG. 6 is a schematic diagram illustrating field distributions for a normalized magnetic field in the XZ plane of a 3 turn circular coil, such as coil antenna 450, with a mean loop diameter of 32 cm and a wire radius of 4.5 mm at a frequency of 5 MHz Collectively, FIGS. 5A, 5B, and 6 illustrate that the strength of the magnetic fields generated by the coil antenna 450 are high at points in close proximity to the wire loops 452, but decrease rapidly at points located farther from the wire loops 452. As noted above, these high magnetic field strengths in close to proximity to the wire loops 452 could potentially damage implants that are to be charged using the coil antenna. Therefore, also as described above, in embodiments of the present invention, a coil safeguard enclosure is disposed around the loops of wire forming a coil antenna. The coil safeguard enclosure is configured to prevent an implant that is be charged from being positioned within a predetermined vicinity of the loops of wire.

In certain embodiments, a coil safeguard enclosure has a symmetrical cross-sectional shape (e.g., circular cross-sectional shape). However, FIGS. 5A and 5B illustrate that an asymmetrical cross-sectional shape (e.g., oval shape with one or two axis of symmetry) may be preferable in certain embodiments. For example, as can be seen from FIGS. 5A and 5B, an asymmetrically shaped coil safeguard enclosure may be more adapted to the H-field where here $H_z<H_x$ for z=10 mm. That is, the Hx components are stronger/higher than the Hz components, thus indicating that it may be preferred to increase the coil safeguard enclosure size in the X plane (horizontal plane), relative to that in the Z plane, to ensure that the implant remains spaced further from the coils in X plane than in the Z plane.

The magnetic field distribution illustrated in FIG. 6 also demonstrates that the oval shaped coil safeguard enclosure may be preferred over a circular cross-sectional shape as the field density is not symmetrical around the wire loops 452. The selected asymmetrical shape may depend, for example, on the loop diameter, the construction of the bundle of wires in the loop, or other factors.

FIGS. 7 and 8 are diagrams illustrating different cross-sectional shapes for coil safeguard enclosures in accordance with embodiments presented herein. Referring first to FIG. 7, shown is a coil safeguard enclosure 760 having a circular cross-sectional shape. Three (3) loops/coils of conductor/wire 753, where the plurality of coils are sometimes collectively referred as a wire-loop bundle 758, are disposed in the coil safeguard enclosure 760. In this embodiment, the coil safeguard enclosure 760 is configured to maintain a substantially equal minimum clearance/distance around the wire-loop bundle 758 in at least the Z and X dimensions/directions. That is, at any discrete location of the wire-loop bundle 758, the coil safeguard enclosure 760 is configured to provide substantially the same minimum clearance around a median point 772 of the wire-loop bundle 758, in at least two dimensions. In the example of FIG. 7, the coil safeguard enclosure 760 has an example diameter of approximately 6 cm and, as such, the minimum clearance from the midpoint 772 of the wire-loop bundle 753 in each of the Z and X directions is approximately 3 cm.

In the embodiments of FIG. 7, an optional electromagnetic compatibility (EMC) screen 766 may be disposed around the coil safeguard enclosure 760. As shown, the EMC screen 766 also has a circular cross-sectional shape and is located at the outer surface 771 of the coil safeguard enclosure 760.

Referring next to FIG. 8, shown is a coil safeguard enclosure 860 having an oval cross-sectional shape that has two axis of symmetry. Disposed in the safeguard enclosure 860 are three (3) loops/coils of conductor/wire 853, where the plurality of coils are sometimes collectively referred as a wire-loop bundle 858. In this embodiment, the coil safeguard enclosure 860 is configured to maintain different minimum clearances/distances around the wire-loop bundle 858 in each of the Z and X dimensions/directions. That is, at any discrete location of the wire-loop bundle 858, the coil safeguard enclosure 860 is configured to provide a minimum clearance around a median or midpoint 872 of the wire-loop bundle 858, in at least two dimensions, but the minimum clearance is different in each of the two dimensions.

In the example of FIG. 8, the coil safeguard enclosure 860 has two axis of symmetry, with a major axis 874 extending along the X-axis and having a length of approximately 6 cm. As such, in the an example of FIG. 8, the minimum clearance from the midpoint 872 of the wire-loop bundle 853 in X-axis directions is approximately 3 cm. The coil safeguard enclosure 860 has a minor axis 876 extending along the Z-axis and having a length that is less than approximately 6 cm. As such, in the example of FIG. 8, the minimum clearance from the midpoint 872 of the wire-loop bundle 853 in the Z-axis directions is less than approximately 3 cm In the embodiments of FIG. 8, an optional electromagnetic compatibility (EMC) screen 866 may be disposed around the coil safeguard enclosure 860. As shown, the EMC screen 866 also has an oval cross-sectional shape with two axis of symmetry and is located at the outer surface 871 of the coil safeguard enclosure 860.

Although FIG. 8 illustrates an oval shape with two axis of symmetry, it is be appreciated that these embodiments are illustrative. In other embodiments, a coil safeguard enclosure may have an oval cross-sectional shape with only one axis of symmetry. In these embodiment, the coil safeguard enclosure is configured to maintain the same minimum distances/volumes around the wire-loop bundle in, for example, each of the Z directions, but different minimum distances/volumes in each of the two X directions.

Figure 9:
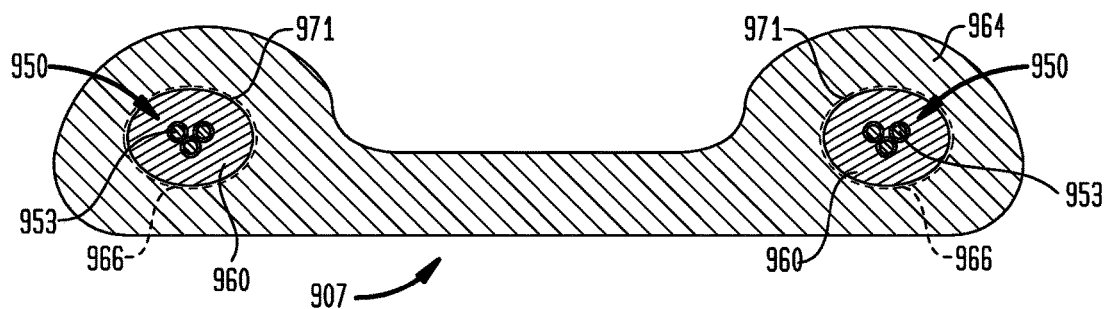
FIG. 9 is a cross-sectional diagram illustrating three loops of wire of an external charger coil assembly implementation, in accordance with certain embodiments presented herein.

As noted above, external chargers in accordance with certain embodiments presented herein may have a number of different arrangements. FIG. 9 illustrates a cross-sectional view of an embodiment in which a coil antenna assembly 907 of an external charger, where the coil antenna assembly 907 is at least partially located within a customized pillow 964. More specifically, a customized pillow 964 is formed from a substantially soft material (e.g., foam) and a coil antenna 950 is disposed therein. The coil antenna 950 is formed by a plurality of coils of wire 953, and a coil safeguard enclosure 960 is disposed around the wires 953 so as to form a minimum clearance around the wires in one or more directions and, accordingly, protect any implant to recharged thereby from one or more of overvoltage or excessive induced current caused by components of the magnetic field in close proximity to the coils of wire. FIG. 9 also illustrates the use of an optional EMC screen 966 located at the outer surface 971 of the coil safeguard enclosure 960.

Figure 10A:
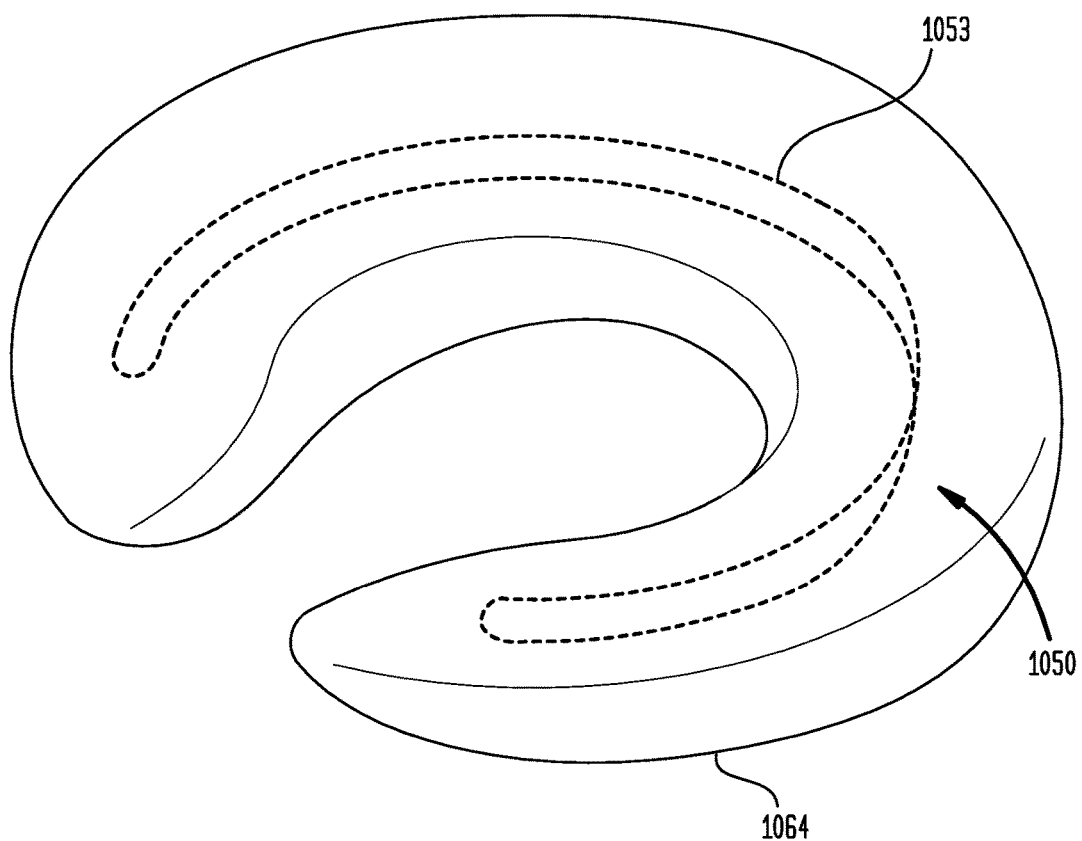
FIG. 10A is a perspective view of an antenna coil assembly of an external charger, in accordance with embodiments presented herein.
Figure 10B:
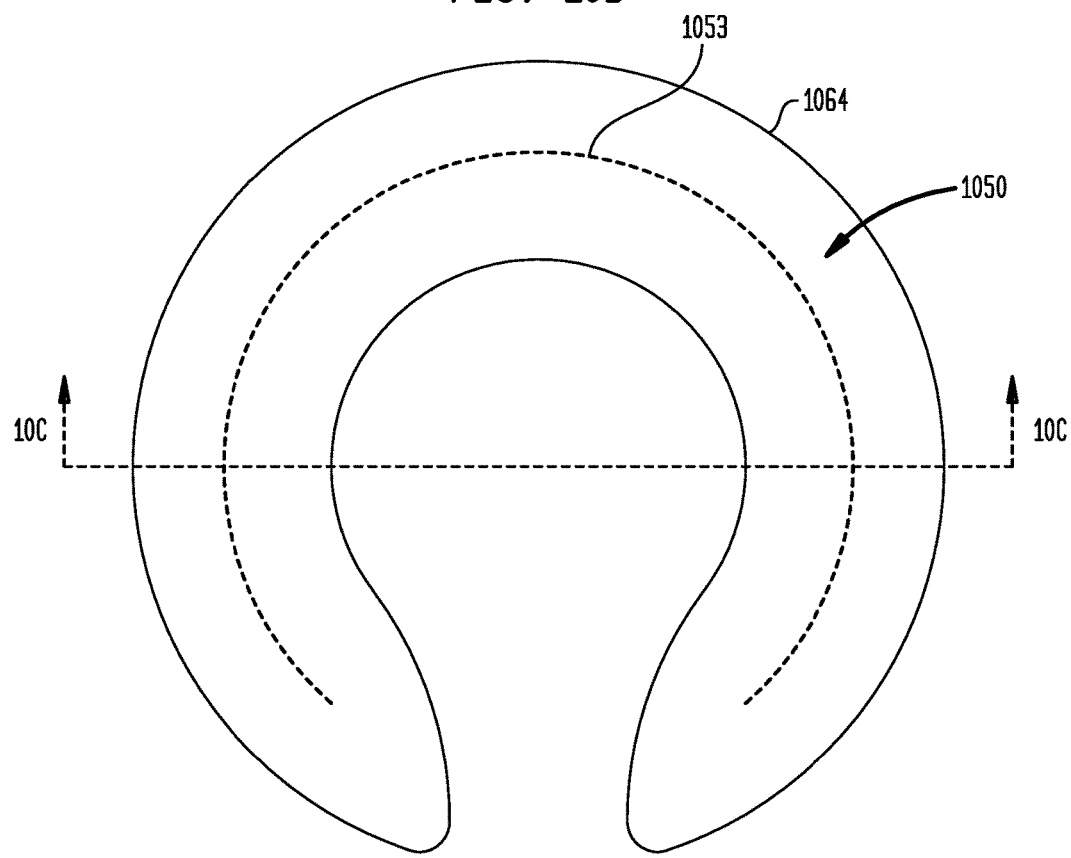
FIG. 10B is a top view of the antenna coil assembly of FIG. 10A.
Figure 10C:
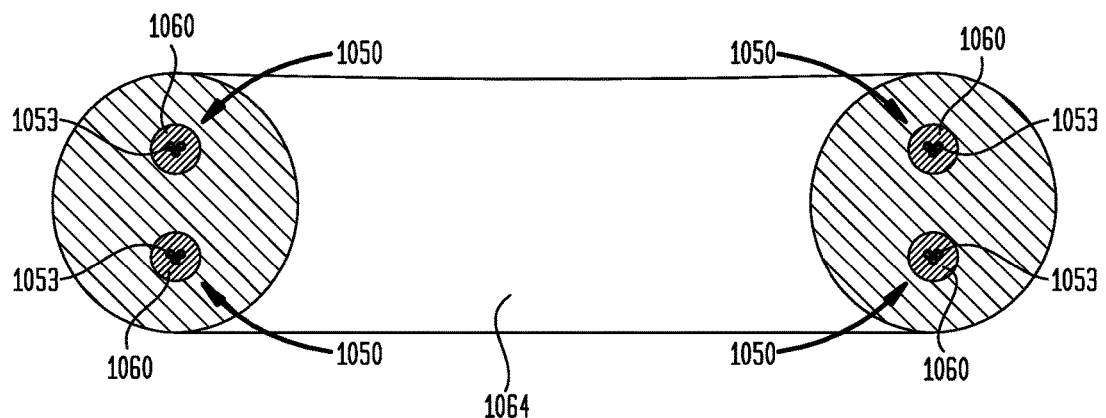
FIG. 10C is a cross-sectional view of the antenna coil assembly of FIG. 10A.

FIG. 10A is a perspective view of a coil antenna assembly 1007 of an external charger, where the coil antenna assembly 1007 is at least partially located within a neck pillow 1064. FIG. 10B is a top view of the coil antenna assembly 1007 and the neck pillow 1064, while FIG. 10C is a cross-sectional view of the coil antenna assembly 1007 and the neck pillow 1064 taken along line 10C-10C in FIG. 10B. For ease of description, FIGS. 10A-10C will be described together.

The neck pillow 1064 is formed from a substantially soft material (e.g., foam) and a coil antenna 1050 is disposed therein. The coil antenna assembly 1007 includes a coil antenna 1050 that is formed by a plurality of coils of wire 1053, and a coil safeguard enclosure 1060 is disposed around the wires 1053 so as to form a minimum clearance in one or more directions around the wires and, accordingly, protect any implant to recharged thereby from one or more of overvoltage or excessive induced current caused by components of the magnetic field in close proximity to the coils of wire. To facilitate understanding of the embodiments of FIGS. 10A-10C, the coil antenna 1050 is shown in FIGS. 10A and 10B using dashed lines.

As noted above, external chargers in accordance with embodiments of the present invention have been primarily described herein with reference to one type of implantable medical device, namely a cochlear implant. It is to be appreciated that the external chargers presented herein may be used with any other partially or fully implantable medical devices now known or later developed, including other auditory prostheses, such as auditory brainstem stimulators, electro-acoustic hearing prostheses, bimodal hearing prostheses, etc., and/or other types of medical devices, such as pain relief implants, pacemakers, etc. As described above, external chargers in accordance with embodiments of the present invention may ensure safe operation for the implant (i.e., prevent overheating or implant component damage. In addition, the external chargers in accordance with embodiments of the present invention may protect the recipient through reduced Specific Absorption Rate (SAR) levels (Specific Absorption Rate) and H-fields and, in certain embodiments, an EMC screen can be provided to reduced radiated emissions It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An external charger for an implantable medical device, comprising:
    at least one coil antenna comprising one or more loops of wire;
    a coil excitation system connected to the at least one coil antenna, wherein the coil excitation system is configured to drive the one or more loops or wire with alternating current to generate a magnetic field that is configured to induce current in at least one implantable coil of the implantable medical device;
    an electrical non-conductive coil safeguard enclosure disposed around the one or more loops of wire to prevent the implantable medical device from being positioned within a predetermined vicinity of the one or more loops of wire; and
    an electromagnetic compatibility (EMC) screen disposed around at least the coil safeguard enclosure.

2. The external charger of claim 1, wherein the coil safeguard enclosure is configured to form a minimum volume around the one or more loops of wire to protect the implantable medical device from one or more of overvoltage or excessive induced current caused by components of the magnetic field in close proximity to the one or more loops of wire.

3. The external charger of claim 1, wherein the coil safeguard enclosure has a circular cross-sectional shape.

4. The external charger of claim 1, wherein the coil safeguard enclosure has an oval cross-sectional shape.

5. The external charger of claim 4, wherein the oval cross-sectional shape has two axis of symmetry.

6. The external charger of claim 4, wherein the oval cross-sectional shape has only one axis of symmetry.

7. The external charger of claim 1, wherein the coil safeguard enclosure is formed from a rigid material.

8. The external charger of claim 1, wherein the coil safeguard enclosure is formed from a partially compressible material having a minimum compressed dimension.

9. The external charger of claim 1, further comprising a compressible base member, wherein the coil safeguard enclosure is at least partially disposed in the base member.

10. The external charger of claim 1, wherein the coil safeguard enclosure includes material with a higher permeability than air that is lossy for harmonics generated by the excitation system above certain frequencies.

11. The external charger of claim 1, further comprising a layer of magnetic material having a higher permeability than air which is disposed between the coil antenna and a support structure, wherein the layer of magnetic material is configured to guide the magnetic field.

12. The external charger of claim 1, further comprising one or more pieces of magnetic material having a higher permeability than air which are disposed in proximity to the coil antenna to guide the magnetic field.

13. The external charger of claim 1, wherein the magnetic field is generated without communication feedback from the implantable medical device.

14. An implantable hearing prosthesis pillow charger, comprising:
    at least one coil antenna configured to emit one or more magnetic fields;
    an electrical non-conductive coil safeguard enclosure disposed around the at least one coil antenna and configured to shield the implantable hearing prosthesis from exposure to densities of the one or more magnetic fields that exceed a predetermined threshold; and
    an electromagnetic compatibility (EMC) screen disposed around at least the coil safeguard enclosure.

15. The implantable hearing prosthesis pillow charger of claim 14, wherein the coil safeguard enclosure is dimensioned so as to prevent the implantable hearing prosthesis from being positioned within a predetermined vicinity of the at least one coil antenna.

16. The implantable hearing prosthesis pillow charger of claim 14, wherein the coil safeguard enclosure has an oval cross-sectional shape.

17. The implantable hearing prosthesis pillow charger of claim 14, wherein the coil safeguard enclosure is formed from a rigid material.

18. The implantable hearing prosthesis pillow charger of claim 14, wherein the coil safeguard enclosure is formed from a partially compressible material having a minimum compressed dimension.

19. The implantable hearing prosthesis pillow charger of claim 14, wherein the coil safeguard enclosure includes material with a higher permeability than air that is lossy for harmonics of the one or more magnetic fields generated above certain frequencies.

20. The implantable hearing prosthesis pillow charger of claim 14, further comprising a layer of magnetic material having a higher permeability than air which is disposed between the coil antenna and a support structure, wherein the layer of magnetic material is configured to guide the magnetic field.

21. The implantable hearing prosthesis pillow charger of claim 20, wherein the layer of magnetic material is a plane structure following the contours of the loop that is configured to improve the magnetic coupling factor between the coil antenna and an implantable coil of the implantable hearing prosthesis.

22. An external charger for an implantable hearing prosthesis implanted in the head of a recipient, comprising:
    at least one coil antenna comprising a wire bundle;
    a coil excitation system configured to drive the one or more loops or wire with alternating current and cause the at least one coil antenna to emit a magnetic field;
    an electrical non-conductive coil safeguard enclosure arranged around the wire bundle and configured to maintain a minimum separation distance between the head of the recipient and the wire bundle; and
    an electromagnetic compatibility (EMC) screen disposed around at least the coil safeguard enclosure.

23. The external charger of claim 22, wherein the coil safeguard enclosure is configured to form a minimum volume around the wire bundle to protect the implantable hearing prosthesis from one or more of overvoltage or excessive induced current caused by components of the magnetic field in close proximity to wire bundle.

24. The external charger device of claim 22, wherein the coil safeguard enclosure has an oval cross-sectional shape.

25. The external charger device of claim 22, wherein the coil safeguard enclosure is formed from a rigid material.

26. The external charger device of claim 22, wherein the coil safeguard enclosure is formed from a partially compressible material having a minimum compressed dimension.

27. The external charger device of claim 22, further comprising a compressible base member, wherein the coil safeguard enclosure is at least partially disposed in the base member.

28. The external charger device of claim 22, wherein the coil safeguard enclosure includes material with a higher permeability than air that is lossy for harmonics generated by the excitation system above certain frequencies.

29. An external charger for an implantable medical device, comprising:
- at least one coil antenna comprising one or more loops of wire;
- a coil excitation system connected to the at least one coil antenna, wherein the coil excitation system is configured to drive the one or more loops or wire with alternating current to generate a magnetic field that is configured to induce current in at least one implantable coil of the implantable medical device;
- an electrical non-conductive coil safeguard enclosure disposed around the one or more loops of wire to prevent the implantable medical device from being positioned within a predetermined vicinity of the one or more loops of wire; and
- a layer of magnetic material having a higher permeability than air which is disposed between the coil antenna and a support structure, wherein the layer of magnetic material is configured to guide the magnetic field.

30. The external charger of claim 29, wherein the coil safeguard enclosure is configured to form a minimum volume around the one or more loops of wire to protect the implantable medical device from one or more of overvoltage or excessive induced current caused by components of the magnetic field in close proximity to the one or more loops of wire.

31. The external charger of claim 29, wherein the coil safeguard enclosure is formed from a rigid material.

32. The external charger of claim 29, wherein the coil safeguard enclosure is formed from a partially compressible material having a minimum compressed dimension.

33. The external charger of claim 29, further comprising a compressible base member, wherein the coil safeguard enclosure is at least partially disposed in the base member.

34. An external charger for an implantable hearing prosthesis implanted in the head of a recipient, comprising:
- at least one coil antenna comprising a wire bundle;
- a coil excitation system configured to drive the one or more loops or wire with alternating current and cause the at least one coil antenna to emit a magnetic field;
- an electrical non-conductive coil safeguard enclosure arranged around the wire bundle and configured to maintain a minimum separation distance between the head of the recipient and the wire bundle; and
- one or more pieces of magnetic material having a higher permeability than air which are disposed in proximity to the coil antenna to guide the magnetic field.

35. The external charger of claim 34, wherein the coil safeguard enclosure is configured to form a minimum volume around the one or more loops of wire to protect the implantable medical device from one or more of overvoltage or excessive induced current caused by components of the magnetic field in close proximity to the one or more loops of wire.

36. The external charger of claim 34, wherein the coil safeguard enclosure is formed from a rigid material.

37. The external charger of claim 34, wherein the coil safeguard enclosure is formed from a partially compressible material having a minimum compressed dimension.

38. The external charger of claim 34, further comprising a compressible base member, wherein the coil safeguard enclosure is at least partially disposed in the base member.

* * * * *